United States Patent
Lippert et al.

(10) Patent No.: US 10,261,300 B2
(45) Date of Patent: Apr. 16, 2019

(54) LIGHT MICROSCOPE AND METHOD FOR IMAGE RECORDING USING A LIGHT MICROSCOPE

(71) Applicant: Carl Zeiss Microscopy GmbH, Jena (DE)

(72) Inventors: Helmut Lippert, Jena (DE); Ralf Netz, Jena (DE); Tiemo Anhut, Jena (DE); Nils Langholz, Apolda (DE); Matthias Langhorst, Hameln (DE)

(73) Assignee: Carl Zeiss Microscopy GmbH, Jena (DE)

( * ) Notice: Subject to any disclaimer, the term of this patent is extended or adjusted under 35 U.S.C. 154(b) by 952 days.

(21) Appl. No.: 14/390,165

(22) PCT Filed: May 16, 2013

(86) PCT No.: PCT/EP2013/060160
§ 371 (c)(1),
(2) Date: Oct. 2, 2014

(87) PCT Pub. No.: WO2013/171309
PCT Pub. Date: Nov. 21, 2013

(65) Prior Publication Data
US 2015/0054937 A1  Feb. 26, 2015

(30) Foreign Application Priority Data
May 16, 2012 (DE) .................. 10 2012 009 836

(51) Int. Cl.
*G01B 9/02* (2006.01)
*G01B 9/04* (2006.01)
(Continued)

(52) U.S. Cl.
CPC ....... *G02B 21/008* (2013.01); *G01B 9/02042* (2013.01); *G01B 9/04* (2013.01);
(Continued)

(58) Field of Classification Search
CPC ... G01N 2021/6419; G01N 2021/6421; G01N 2021/6463; G02B 21/008; G02B 21/0028;
(Continued)

(56) References Cited

U.S. PATENT DOCUMENTS 5,737,121 A   4/1998 Dixon
5,825,533 A  10/1998 Yonezawa
(Continued)

FOREIGN PATENT DOCUMENTS

CN   101680749 A   3/2010
CN   102575928 A   7/2012
(Continued)

OTHER PUBLICATIONS

Krzewina, "Single-exposure optical sectioning by color structured illumination microscopy", Optics Letters, Feb. 15, 2006, 3 pages.
(Continued)

*Primary Examiner* — Edemio Navas, Jr.
*Assistant Examiner* — William Adrovel
(74) *Attorney, Agent, or Firm* — LaBatt, LLC (57) ABSTRACT

The invention relates to a light microscope comprising a polychromatic light source for emitting illumination light in the direction of a sample, focussing means for focussing illumination light onto the sample, wherein the focussing means, for generating a depth resolution, have a longitudinal chromatic aberration, and a detection device, which comprises a two-dimensional array of detector elements, for detecting sample light coming from the sample. According to the invention, the light microscope is characterized in that, for detecting both confocal portions and non-confocal portions of the sample light, a beam path from the sample to the detection device is free of elements for completely (Continued)

masking out non-confocal portions. In addition, the invention relates to a method for image recording using a light microscope.

18 Claims, 3 Drawing Sheets

(51) Int. Cl.
*G01N 21/64* (2006.01)
*G02B 21/00* (2006.01)
*G02B 21/08* (2006.01)
*G02B 21/14* (2006.01)
*G02B 21/18* (2006.01)
*G02B 21/24* (2006.01)
*G02B 21/36* (2006.01)

(52) U.S. Cl.
CPC ....... *G02B 21/006* (2013.01); *G02B 21/0028* (2013.01); *G02B 21/0032* (2013.01); *G02B 21/0044* (2013.01); *G02B 21/0064* (2013.01); *G02B 21/0068* (2013.01); *G02B 21/0092* (2013.01); *G02B 21/08* (2013.01); *G02B 21/14* (2013.01); *G02B 21/18* (2013.01); *G02B 21/367* (2013.01); *G01B 2210/50* (2013.01); *G01N 2021/6419* (2013.01); *G01N 2021/6421* (2013.01); *G01N 2021/6463* (2013.01); *G02B 21/0036* (2013.01); *G02B 21/24* (2013.01)

(58) Field of Classification Search
CPC ...... G02B 21/367; G02B 21/18; G02B 21/24; G02B 21/0032; G02B 21/0036; G02B 21/0044; G02B 21/006; G02B 21/0064; G02B 21/0068; G02B 21/0092; G02B 21/08; G02B 21/14; G01B 9/02042; G01B 9/04; G01B 2210/50
See application file for complete search history.

(56) References Cited

U.S. PATENT DOCUMENTS

| | | | |
|---|---|---|---|
| 6,399,935 B1 | 6/2002 | Jovin et al. | |
| 6,628,385 B1* | 9/2003 | Osipchuk | G02B 21/002 250/458.1 |
| 2002/0141051 A1* | 10/2002 | Vogt | G02B 21/0036 359/385 |
| 2003/0063379 A1* | 4/2003 | Fukuyama | G02B 21/0032 359/390 |
| 2004/0109170 A1 | 6/2004 | Schick | |
| 2004/0149883 A1* | 8/2004 | Eda | G01B 11/0608 250/201.3 |
| 2007/0014001 A1 | 1/2007 | Ujike et al. | |
| 2007/0041089 A1* | 2/2007 | Lauer | G02B 21/0032 359/369 |
| 2007/0205378 A1* | 9/2007 | Tomioka | G02B 21/0064 250/458.1 |
| 2010/0099984 A1 | 4/2010 | Graser | |
| 2010/0108873 A1 | 5/2010 | Schwertner | |
| 2011/0043661 A1* | 2/2011 | Podoleanu | A61B 3/102 348/239 |
| 2011/0080576 A1 | 4/2011 | Thiel et al. | |
| 2011/0300490 A1* | 12/2011 | Rachet | G02B 21/0032 430/322 |
| 2012/0156636 A1 | 6/2012 | Stock et al. | |
| 2013/0015366 A1* | 1/2013 | Hayashi | G01N 21/6458 250/458.1 |
| 2013/0050711 A1 | 2/2013 | Ertl | |
| 2013/0100405 A1* | 4/2013 | Porter | A61B 3/1015 351/206 |
| 2013/0182096 A1* | 7/2013 | Boccara | A61B 5/0066 348/79 |
| 2014/0043460 A1* | 2/2014 | Hartell | G02B 17/0615 348/79 |
| 2014/0313576 A1* | 10/2014 | Uhl | G02B 21/14 359/385 |

FOREIGN PATENT DOCUMENTS

| | | |
|---|---|---|
| DE | 10327987 | 1/2005 |
| DE | 102006019952 | 1/2007 |
| DE | 102007018048 A1 | 10/2008 |
| DE | 102007019267 A1 | 10/2008 |
| DE | 102010036447 | 9/2011 |
| EP | 0911667 | 4/1999 |
| EP | 1398597 | 3/2004 |
| JP | H09325279 A | 12/1997 |
| JP | 2001091842 A | 4/2001 |
| JP | 2004101532 A | 4/2004 |
| JP | 2010026344 A | 2/2010 |
| JP | 2010525404 A | 7/2010 |
| WO | 2009121922 | 10/2009 |
| WO | 2010130843 | 11/2010 |
| WO | 2012035170 A1 | 3/2012 |

OTHER PUBLICATIONS

Wicker, "Single-shot optical sectioning using polarization-coded structured illumination", Journal of Optics, Jul. 15, 2010, 9 pages.
Mitie, "Optical sectioning in a wide-field microscopy obtained by dynamic structured light illumination and detection based on a smart pixel detector array", Optics Letters, May 1, 2003, 3 pages.
Vogel, "Structured-illumination microscopy on technical surfaces: 3D metrology with nanometer sensitivity",Institute of Optics at University of Erlangen-Nuremberg, 2011, 6 pages.
Tiziani, "Confocal principle for macro and microscopic surface and defect analysis", Optical Engineering, Jan. 2000, 8 pages.
Papastathopoulos, Chromatic confocal spectral interferometry, Applied Optics, Nov. 10, 2006.
Lin, "Single-shot depth-section imaging through chromatic slit-scan confocal microscopy", Applied Optics, Oct. 1, 1998.
Mertz, "Scanninglight-sheet microscopy in the whole mouse brain HiLo background rejection", Journal of Biomedical Optics, Jan./Feb. 2010, 7 pages.
Rahlves, "Optisches Messen technischer Oberflachen", 3 pages.
International Search Report for PCT Application No. PCT/EP2013/060160 with English translation, dated Dec. 25, 2013, 10 pages.
International Preliminary Report on Patentability for PCT Application No. PCT/EP2013/060160 with English translation, dated Nov. 18, 2014, 18 pages.
Chinese Application No. 201380025813X, First Office Action (including English translation), dated Jul. 5, 2016, 22 pages.
Davidson, C., Application No. GB1417062.5, Examination Report, dated Jun. 9, 2017, 5 pages.
Tonooka, M., Application No. 2015-512065, Notice of Grounds for Rejection (Only the English translation is available.), dated May 9, 2017, 2 pages.
Yang, J., Application No. 201380025813.X, Notification of the Second Office Action (Only the English translation is available.), dated Mar. 3, 2017, 14 pages.

* cited by examiner

LIGHT MICROSCOPE AND METHOD FOR IMAGE RECORDING USING A LIGHT MICROSCOPE

The invention relates in a first aspect to a light microscope according to the preamble to claim 1.

In a further aspect the invention relates to a method for recording images with a light microscope according to the preamble to claim 16.

Confocal microscopy is used today as the standard method for characterising technical surfaces and in particular for deriving roughness measurement values and topographies. This method is described for example in: M. Rahlwes, J. Seewig: "Optisches Messen technischer Oberflächen", Beuth Publishing House, Berlin, 2009.

In many confocal systems, scanning of the specimen takes place in all three spatial directions, that is to say: on the one hand, there are point-scanning systems, wherein an optical beam is guided in x/y-direction over the specimen. In order to derive the height information, on the other hand, it is necessary to move the specimen relative to the detector unit, thus in the z-direction. The height information and hence the topography for each x-y location can be derived from the intensity maximum in dependence upon the z-position. A disadvantage of this method is on the one hand the long time required by the scan for a 3D topography. On the other hand, a further disadvantage is that the precision, thus the accuracy, of the height measurement is highly dependent upon the adjustment accuracy of the specimen surface relative to the detector unit and is therefore always limited. In other words: a high precision requires highly accurate and expensive mechanical adjusting elements, for example on a piezo basis.

In order to avoid the disadvantage of the x-y scan, confocal wide-field systems have already existed for a long time, wherein area cameras are generally used and which thus have a high degree of parallelisation. An example of this is the spinning disc method with a Nipkow disc which is also described in the publication by Rahlwes and Seewig. Here, a plurality of points are simultaneously detected according to the confocal principle. Instead of a Nipkow disc, a rapid-switching microdisplay can also be used in principle. In addition a multi-line scan can be carried out with digital-confocal detection. All these systems work truly confocally, that is to say: essentially only light from the excitation focus is detected. This results in a certain degree of complexity of the apparatuses and methods used. In addition, on account of the fixed elements used, in particular thus a microdisplay with defined pixel size or a Nipkow disc with a defined hole size, the technologies offer limited flexibility having regard to different field of view sizes and, in association therewith, different z-sensitivities. In addition, as in the case of the point-scanning systems, scanning of the specimen in z-direction is also necessary here.

Having regard to complexity and flexibility, the confocal wide-field systems based upon structured illumination offer advantages over the above. Here, for each z-value, a confocal cross-sectional image is calculated from images which have been recorded with a structured illumination produced for example through a grating. Generally, the wide-field image can thereby also be obtained. A pinhole array is not required in the detection. For example, an illumination grating with different phase positions can be imaged onto the specimen. Since intensity modulations are present, in dependence upon the phase position, only for focal image portions, a cross-sectional optical image can be calculated therefrom. This method has been examined, for example in Vogel et al. Pwroc. DGaO 2011, P36, for the measurement of technical surfaces. A similar approach, which is described for example in DE 10 2007 018 048 A1, uses only two grating phases in the illumination. According to another related method, a continuously changing structured illumination is used and the cross-sectional optical image is calculated from two images recorded in parallel, wherein one contains outer focal and focal portions and the other contains only outer focal portions. An advantage of this method based upon structured illumination is that a wide-field image can also be obtained in parallel with the confocal image. The problem remains, however, that the specimen must be scanned in z-direction relative to the detector.

A particular configuration of confocal cross-sectional image production with structured illumination is described in Mitic et al., Optical Letters 28, 698 (2003). Here, apart from a movable grating, a so-called smart pixel detector array is used which allows the time-modulated signal portions and hence the focal signal portions to be extracted in real time directly on the detector plane.

Further particular configurations of structured illumination are described in Wicker et al., Journal of Optics 12, 084010 (2010) and Krzewina et al., Optical Letters 31, 477 (2006).

Here, the different grating phases are applied quasi in parallel to the specimen with the aid of polarisation encoding or, respectively, colour encoding, which is associated above all with speed advantages.

There are further wide-field methods, with which optical sections can be produced. On the one hand the so-called focus variation is to be mentioned, wherein the image sharpness is evaluated in dependence upon the z-coordinate in order to calculate a maximum therefrom, similarly to the confocal case. Spatial information is thus also used. The method described in Mertz et al., Journal of Biometrical Optics, 15, 016027 (2010) is to be similarly categorised, wherein wide-field images are recorded with and without structuring in order to obtain therefrom a cross-sectional optical image through the proficient use of spatial band-pass filters. The structuring can thereby also be based upon a so-called speckle pattern.

The so-called chromatic confocal principle is also tried and tested for the purpose of avoiding scanning in z-direction. Here, in general, a polychromatic light source is used which illuminates the specimen of interest via a chromatically effective refractive or diffractive element, whereby the z-information is spectrally encoded. If the spectrum is measured behind a confocal pinhole in the detection, the height information can be derived therefrom. It is also possible to use a tunable light source with sequential confocal detection, whereby a spectrum is likewise obtained. In most cases, commercial sensors are point detectors which always have the disadvantage of the lack of x-y parallelisation. A chromatic multifocal arrangement with a pinhole array is described for example in DE 10 2007 019 267 A1. However, the focal points only partially cover the field of view, meaning that a scanning movement continues to be necessary. In addition there are line-scanning systems, described for example in Lin et al., Applied Optics 37, 6764 (1998), and systems based upon a Nipkow disc—see for example Tiziani et al., Opt. Eng. 39, 32 (2000). The latter have, however, to date always been realised with colour camera systems which only facilitate a limited height resolution and also exhibit difficulties in the case of colour objects, because an overlaying of height and colour information or, respectively, spectral reflectivity arises here. In this connection, an interesting approach involves a multifocal chromatic arrangement being realised with the aid of a DMD (Digital Micromirror Device). A tunable titanium-sapphire laser is used here, with which the chromatic height scan is carried out. In combination with a switching of the DMD, a structure is thus realised which allows highly accurate 3D topography data without any mechanical movement elements. However, image artifacts can arise here through the DMD and the switching speed of the DMD is generally limited. Furthermore, a wide-field image cannot be obtained in parallel.

A further development of the chromatic confocal point sensor is the so-called chromatic confocal spectral interferometry, described for example in Papastathopoulos et al., Applied Optics 45, 8244 (2006). Here, an interferometer structure is realised in addition to the chromatic confocality. Such a structure can also be regarded as a white light interferometer with extended depth of field. Besides the spectral maximum, the spectral phase can also be evaluated here, in which height information is likewise contained.

It has been mentioned above that the chromatic confocal wide-field methods have been realised to date essentially using a tunable light source or a colour camera. In the meantime, multiple approaches have become available for spectral wide-field image production with high resolution. For example there are FTT (Fast Fourier Transformation) spectrometer systems, wherein the spectrum is derived from wavelength changes in an interferometer structure and subsequent Fourier analysis. Furthermore there is the "Image Slicing Spectrometer" technology, wherein individual image portions are imaged offset relative to each other on a large area sensor in such a way that gaps are produced which can be used to obtain the spectral information by means of a dispersive element arranged upstream. Prior art also exists relating to a combination of such a spectrometer with a 3D image production in the sense of a structured illumination.

In addition, 3D Bragg gratings are used to obtain hyperspectral recordings with high spatial and spectral resolution through the sequential recording of monochromatic images.

A combination of these technologies with a chromatic confocal wide-field system is not known to date.

A generic light microscope has a polychromatic light source to emit illuminating light in the direction of a specimen and focussing means to focus illuminating light onto the specimen, wherein the focussing means have a longitudinal chromatic aberration to produce a depth resolution. A generic light microscope additionally comprises a detection unit which has a two-dimensional array of detector elements to detect specimen light coming from the specimen.

It is provided according to a generic method for recording images with a light microscope that illuminating light is transmitted with a polychromatic light source in the direction of a specimen, that the illuminating light is focussed onto the specimen with focussing means, wherein a depth resolution is achieved through a longitudinal chromatic aberration of the focussing means, and that specimen light coming from the specimen is detected with a detection unit comprising a two-dimensional array of detector elements.

A disadvantage of known light microscopes and methods is that only a proportion of the information which can be obtained via the illuminating light emitted by the light source to the specimen is used.

It can be regarded as an object of the invention to provide a light microscope which facilitates the measurement of additional information for a microscopic specimen. In addition a method for recording images with a light microscope shall be described, with which additional information for a microscopic specimen can be obtained.

This object is achieved through the light microscope having the features of claim 1 and through the method having the features of claim 16.

Advantageous embodiments of the light microscope according to the invention and preferred variants of the method according to the invention are the subject matter of the dependent claims and are additionally described in the following description, in particular in connection with the figures.

It is provided according to the invention for the light microscope of the abovementioned type that an optical path from the specimen to the detection unit is free of elements for complete filtering-out of non-confocal portions in order to detect both con-focal portions and also non-confocal portions of the specimen light.

According to the method of the abovementioned type, both con-focal portions and also non-confocal portions of the specimen light are guided onto the detection unit according to the invention.

It can be regarded as a core idea of the invention that non-confocal portions of the specimen light, which are filtered out in confocal microscopes according to the prior art, are detected at least partially with the detection unit. Confocal portions of the specimen light are to be understood to be the portions coming from a plane of a focus of the illuminating light in or on the specimen. This plane can be defined perpendicularly to the optical axis of the light microscope.

Non-confocal portions of the specimen light are to be correspondingly understood to be those portions of the specimen light coming from a plane other than the focal plane of the illuminating light. In known confocal microscopes, these light portions are filtered out. It is known in this connection to arrange a pinhole, that is to say: a diaphragm with a small circular or slit-form passage, at a plane conjugated with the specimen plane under examination. Instead of the pinhole, the structured element can also be used for this purpose. In contrast, according to the invention the non-confocal light portions are not filtered out or are only partially filtered out. It is advantageously thereby possible to create a wide-field image of the specimen from the detected specimen light. A wide-field image is to be understood within the meaning of the invention to be an image, for which both specimen light from the focal plane of the illuminating light and also specimen light coming from regions outside of the focal plane of the illuminating light are used. In addition, suitable means can be present to create a confocal image of the specimen, wherein exclusively the confocal portions of the specimen light are shown.

A large information content, in particular both a confocal image and also a wide-field image, can thus advantageously be obtained through a single measurement or a single measurement sequence, whereby mechanical movements of components of the light microscope are not necessary or are only necessary to a limited extent.

The illuminating light can be understood to be any light which is radiated towards the specimen. The illuminating light can be monochromatic or can also comprise one or more wavelength ranges. Specimen light, on the other hand, is understood to be light which is emitted by the specimen as a result of the radiation of illuminating light onto this specimen. The specimen light can thus be illuminating light that is radiated back, in particular scattered and/or reflected. However, the specimen light can also have been produced through intrinsic luminescence, in particular through fluorescence or through phosphorescence.

The polychromatic light source can comprise for example one or more tunable lasers. Alternatively or additionally, the light source can comprise a white light source, a halogen lamp and/or a diode, in particular a superluminescent diode. The illuminating light can lie for example in the infrared range, in the visible wavelength range or in the ultraviolet range.

According to a preferred embodiment of the light microscope according to the invention, a structured element is located between the light source and the focussing means to produce structured illuminating light from the illuminating light emitted by the light source. Here, the focussing means thus guide structured illuminating light onto the specimen.

The structured element can be understood to be in principle any element, with which a certain spatial structure is imprinted on the illuminating light at the specimen plane. The structured element can preferably comprise a Nipkow disc, a microlens array, a grating, in particular a 1D grating or 2D grating, a Fresnel bi-prism or an element for generating a speckle pattern. In the case of a grating or an element for generating a speckle pattern, the illuminating light comprises coherent portions or is completely coherent. A speckle pattern is to be understood to be a seemingly random pattern produced through interference of coherent light waves which are diffracted at an irregularly structured element.

An essential advantage of this embodiment can be regarded as being that a large number of different xyz-regions of the specimen can be examined simultaneously or shortly one after the other. Different z-positions can thus be imaged via the wavelength-dependent focal position. Advantageously, no scanning movement is necessary here, thus no displacement of the specimen relative to an objective of the light microscope. In addition, different xy-ranges of the specimen can be examined via the structured element without a scanning movement being required. Depending upon the design of the structured element, different xy-ranges can be imaged simultaneously, for example in the case of a grating as a structured element, or one after the other, as in the case of a rotating pinhole or a Nipkow disc as a structured element. In both cases, displacement of the specimen relative to the objective is advantageously not necessary.

In order to ensure that non-confocal portions of the specimen light also reach the detection unit, according to a preferred embodiment of the light microscope according to the invention a beam splitter is present between the structured element and the specimen which is permeable to illuminating light and reflective for specimen light coming from the specimen, or vice versa. It is hereby possible to prevent specimen light from having to pass through the structured element on its way to the detection unit. In particular, if the structured element has such dimensions that it filters out non-confocal light portions, non-confocal portions of the specimen light can hereby advantageously still reach the detection unit. An illumination of the specimen necessary for confocal microscopy can simultaneously be provided here. Filtering-out of non-confocal portions of the specimen light can arise for example in the case of a Nipkow disc as a structured element if the holes thereof are of a size which is smaller than or the same as those of an Airy disc. The Airy disc thereby constitutes the minimum illuminating disc, due to diffraction, at the focus of the illuminating light on the specimen.

The beam splitter is preferably a polarisation beam splitter, and means for changing the polarisation direction of light are present between the polarisation beam splitter and the specimen location in order to change the polarisation direction of specimen light and thus to forward/to guide specimen light to the detection unit. These means can be formed for example with a λ/4 plate, with which illuminating light travelling towards the specimen and specimen light coming from the specimen are respectively rotated in the polarisation direction. As a result, the polarisation direction of the illuminating light and the polarisation direction of the specimen light are perpendicular to each other at the polarisation beam splitter. A spatial separation of the illuminating light and the specimen light can thereby be efficiently achieved. A polarisation filter can usefully be present between the light source and the polarisation beam splitter, so that only polarised illuminating light impinges on the polarisation beam splitter and subsequently on the specimen.

In order to filter out stray light, of which the polarisation direction does not coincide with the polarisation direction of the specimen light to be detected, a further polarisation filter can be present between the polarisation beam splitter and the detection unit. Alternatively or additionally to the polarisation beam splitter, it is provided according to a further preferred variant that specimen light coming from the specimen is guided through the structured element onto the detector unit and that structures of the structured element are sufficiently large to allow the passage of non-confocal portions of the specimen light. These structures can for example be hole diameters of a Nipkow disc, lens diameters of a microlens array or the periodicity constant of a grating. In an arrangement of the structured element in a plane conjugated with the specimen plane, these structures can be sufficiently large if they are larger than the Airy disc, preferably at least twice or three times the size of the Airy disc. The Airy disc defines the cross-sectional area of the illuminating light at the focus on the specimen. The diameter of the Airy disc can be defined as 1.2 times the wavelength of the illuminating light divided by the numerical aperture of the objective.

It is provided according to a further preferred embodiment of the light microscope according to the invention that the structured element is mirrored on one side, wherein specimen light coming from the specimen is guided onto the mirrored side of the structured element and partially reflected and partially transmitted there, that the detection unit has a first and a second detector, that the first detector is arranged to measure specimen light coming from the specimen and transmitted at the structured element, and that the second detector is arranged to measure specimen light coming from the specimen and reflected at the structured element. It can hereby be provided in particular that a confocal optical path is achieved through the structured element. In this case, a confocal image of the specimen can be recorded with specimen light transmitted at the structured element, wherein non-confocal light portions have been filtered out at the structured element. On the other hand the specimen light reflected at the structured element also has non-confocal portions in this case, so that a wide-field image of the specimen can be produced therewith.

The focussing means can be part of an objective or comprise an objective. In order to produce a wavelength-dependent focal position, the focussing means have according to a preferred embodiment a refractive and/or a diffractive microlens array, i.e., a two-dimensional arrangement of microlenses. Through the longitudinal chromatic aberration of the focussing means, the position of the focus along the optical axis depends upon the wavelength of the illuminating light. Broadband illuminating light or illuminating light with different spectral portions is therefore focussed onto different depths along the optical axis. This facilitates the recording of images of the specimen at different depths or z-values without a mechanical adjustment of the light microscope being necessary. A plurality of specimen points which are adjacent to each other in a plane which is transverse to the optical axis can advantageously be simultaneously examined with a microlens array. This xy-plane can also be imaged without a scanning movement. A high degree of parallelisation is thereby achieved, wherein a large number of different xyz-regions of the specimen can be recorded simultaneously or alone by moving the structured element.

For a particularly high resolution in the z-direction via the chromatic aberration of the focussing means, a knowledge which is as accurate as possible and selection of the light wavelength are desirable. For this, on the one hand the specimen light coming from the specimen can be detected with spectral resolution. On the other hand, for this purpose, alternatively or additionally, different spectral ranges of the illuminating light of the light source can be sequentially guided onto the specimen. It is provided according to a preferred embodiment that a wavelength selection unit is present to select a variably adjustable spectral range of the illuminating light in order to focus illuminating light, via the focussing means, onto different positions along the optical axis, and that electronic control means are present to select a spectral range by means of the wavelength selection unit. The wavelength selection unit preferably has a prism, a grating, a colour filter and/or an acousto-optic tunable filter (AOTF).

Shorter measurement times and fewer mechanical movements are achieved according to a variant, wherein the structured element, for example a grating, can be illuminated from two sides, so that two phases of the structured element can be imaged onto the specimen plane. This is particularly desirable if a plurality of images are recorded with different phases of the structured element and taken into calculation using the Moiré effect to form a single image with improved resolution. It is thereby provided that a deflection means is present for electively guiding illuminating light onto a first or a second light path and that the structured element is mirrored on one side, wherein illuminating light of the first light path is guided onto the mirrored side of the structured element and is reflected at the structured element in the direction of the specimen, wherein illuminating light of the second light path is guided onto another side of the structured element and transmitted by the structured element in the direction of the specimen, and wherein the transmitted illuminating light and the reflected illuminating light produce images of the structured element on the specimen with phase displacement relative to each other.

It is preferable for the deflection means to have a switchable mirror, in particular a galvanometer mirror, a micromirror actuator (DMD, digital micromirror device) or a micro-electromechanical system (MEMS), an acousto-optic modulator (AOM), an acousto-optic deflector (AOD), an electro-optic modulator (EOM) or a switching unit based upon a polarisation rotation. At least one respective optical fibre can be present to guide illuminating light along the first and/or second light path.

Alternatively or additionally to providing the two light paths, a shifting of the structured element can be realised by means of the deflection means. For this, it is provided according to a preferred variant of the light microscope according to the invention that positioning means are present to displace and/or rotate the structured element and that electronic control means are present which are adapted to record images of the specimen at different positions of the structured element with the detection unit and to take the images into calculation to form one specimen image. It is preferable for the detection unit to be a spectrally resolving detection unit. Here, specimen light portions of differing wavelengths can advantageously be simultaneously detected and distinguished from each other. An improvement in the z-resolution can thereby be achieved.

The detection unit can be in particular a smart pixel array detector, thus an area detector chip with a computer unit on the chip, with which a demodulation calculation of the signals received is possible directly at the detector. In order to produce the spectral resolution of the detection unit, spectral filtering means can be present, in particular an acousto-optic tunable filter (AOTF), a prism, a grating and/or at least one colour filter. Alternatively, the detection unit can have an interferometer.

It is provided according to a preferred variant of the method according to the invention that, for the determination of a height profile of a specimen, images of the specimen are recorded which differ in the detected wavelength range of the specimen light, that a modulation contrast for image points of each image is determined, that the image point is selected, from the image points having the same position in the different images, which has the greatest modulation contrast, and that height information of the specimen is assigned to the selected image point in dependence upon the associated wavelength range, wherein respective height information has been previously stored for each of the different wavelength ranges. An image of the specimen can hereby be recorded with a single position of the structured element or be calculated by taking into calculation a plurality of images which are recorded at different positions or different phases of the structured element. The modulation contrast can be understood in the simplest case to be a brightness difference between adjacent image points in the same image. Illuminating light which, due to its wavelength, is focussed by the focussing means directly onto a specimen surface to be examined produces a sharp image of the specimen with high modulation contrast. Illuminating light of a different wavelength produces on the other hand a blurred image which has a low modulation contrast. In particular a pattern can be imaged on the specimen surface via the structured element which has differing sharpness in dependence upon the wavelength of the illuminating light. The modulation contrast is thus based upon the sharpness of the imaging of the structured element on the specimen surface. Since the height of the specimen surface can depend upon the xy-position of the different specimen regions, determination and comparison of the modulation contrast is realised for a multitude of xy-regions within an image, preferably for each image point.

In embodiments described thus far, a z-resolution is achieved by splitting up the focuses for different wavelengths. In addition, however, the phase position of the illuminating light on the specimen surface can also be used which depends upon the distance of the specimen from the objective and therefore upon the height profile of the specimen. To this end, a spectral interferometry can be carried out. Illuminating light of a known wavelength is thereby guided onto the specimen. Specimen light is partially guided back onto the specimen with an interferometer so that it can constructively interfere there. For this, a length of an interferometer reference path must be suitably adjusted with the interferometer, which depends upon the distance from the specimen surface. This length to be set thus contains information for the specimen profile. It can accordingly be provided in a preferred method variant that, with an interferometer, in particular a Linnik interferometer, a part of the specimen light is guided onto a reference path with adjustable length and subsequently guided back onto the specimen, wherein, on a surface of the specimen, a constructive interference between illuminating light and specimen light guided back depends upon a height profile of the specimen and upon the length of the reference path, that the length of the reference path is varied and the length is selected, at which a maximum signal is received with the detection unit, and that the height profile of the specimen is concluded from the selected length of the reference path with the aid of previously stored values.

An exact knowledge of the wavelength of the detected light is necessary for this purpose.

It is provided in particular for this purpose according to a further preferred method variant that a wavelength selection is realised both via spectral filtering means of the detection unit and also via a wavelength selection unit at the light source in order to improve the spectral resolution. The z-resolution is hereby advantageously further improved and an interferometer can be meaningfully used as described above.

In order to create a confocal image of the specimen without mechanical filtering-out of non-confocal light portions being necessary, it is provided according to a preferred variant of the method according to the invention that the detector elements are used as a digital diaphragm to produce a confocal image, wherein, for the creation of the confocal image, those detector elements are used, onto which specimen regions lying in the focus of the illuminating light are sharply imaged. The detection unit is preferably arranged in a plane which is conjugated with the specimen plane. Detector elements, on which solely non-confocal light portions impinge, are not hereby used. Alternatively, information of these detector elements can be used to estimate and subtract the non-confocal light portion on the remaining detector elements, on which the confocal light portions are imaged. According to this embodiment, a wide-field image of the specimen with the non-confocal and the confocal portions of the specimen light can additionally or alternatively be calculated.

According to a variant of the method according to the invention, a so-called HiLo method can be used. It is provided herein that a first image of the specimen is recorded, wherein a structured element is located in the optical path to produce a structured illumination, that a second image is recorded to examine specimen regions which in particular were not illuminated with the structured illumination when recording the first image, wherein the structured element is not located in the optical path, and that the first and the second image are taken into calculation to form a specimen image. The different information which can be obtained with and without the use of a structured element is hereby brought together.

In order to determine a height profile of a specimen or to distinguish different measurement depths it can be provided that specimen light is detected with spectral resolution and a sharpness function is determined via the wavelength. The wavelength, at which there is maximum sharpness, can be determined therefrom as the specimen height. This corresponds to the principle of focus variation and allows a very high depth resolution.

A measurement resolution in a specimen plane which lies transversely to an optical axis can be further improved in a method variant, wherein a polarisation encoding of illuminating light and/or specimen light takes place. It is hereby provided that regions lying one beside the other in the specimen plane are irradiated with illuminating light of different polarisations or that a location-dependent specimen light polarisation is carried out, wherein a certain polarisation is imprinted on the specimen light in dependence upon its position transversely to the optical axis. Specimen light for different polarisations is then separately detected and location information within the specimen plane is assigned to the detected specimen light in dependence upon its polarisation.

For example, illuminating light or specimen light can be distinguished as having left circular and right circular polarisation. Alternatively, however, different linear polarisations can also be used as a distinguishing feature. In order to produce a spatial structure of the polarised illuminating light in the specimen plane, additional optical elements, for example one or more gratings, can be arranged in the optical path.

In principle, a resolution improvement can also be realised in the specimen plane, instead of or in addition to a polarisation encoding, through a colour encoding. Illuminating light is thereby transmitted in dependence upon its wavelength onto different specimen regions or specimen light is filtered in dependence upon its position transversely to the optical axis. Different wavelengths of the detected light can then be assigned to different xy-values in the specimen plane. For a depth resolution, optical means with a longitudinal chromatic aberration can usefully be omitted in this embodiment. Instead, a different light property can be used for depth encoding, for example the polarisation of the light to be detected.

The light microscope according to the invention is preferably adapted to carry out the method according to the invention and the method variants.

Further features and advantages of the invention are described below by reference to the attached schematic drawing, in which.

The same components and those having the same effect are generally identified in the figures with the same reference signs.

Figure 1:
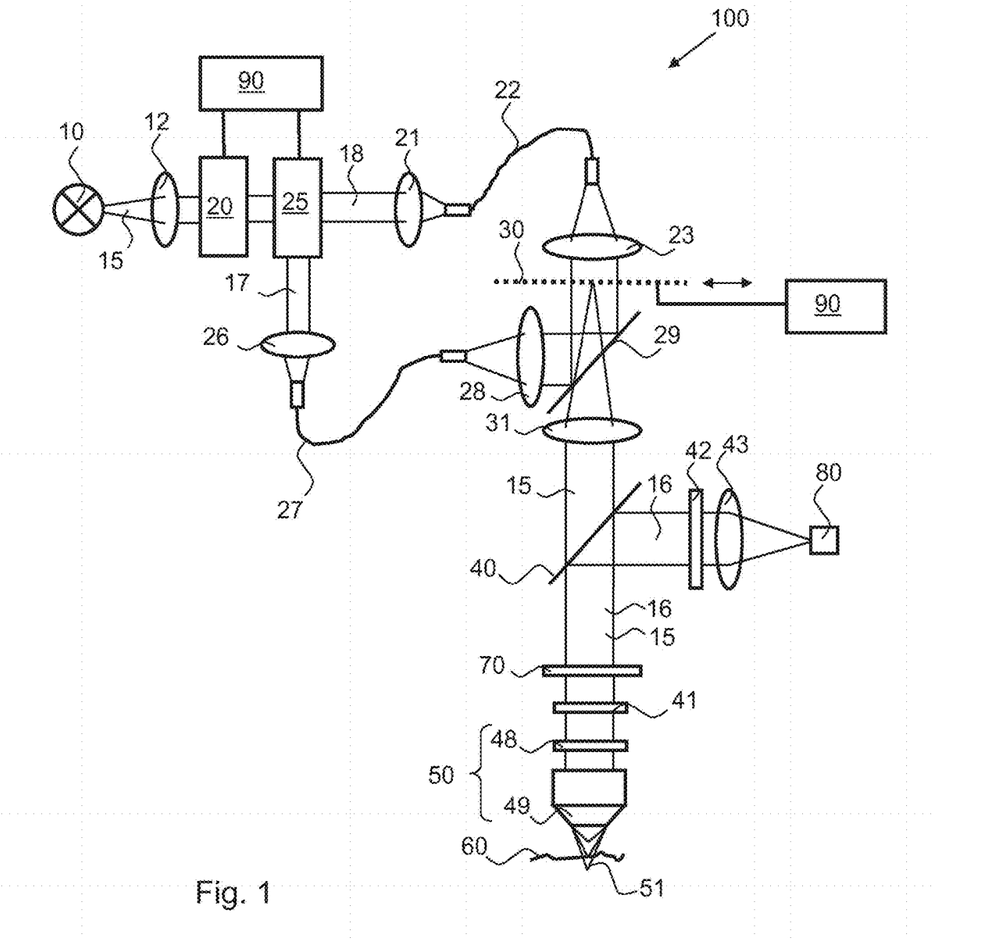
FIG. 1 shows a schematic illustration of a first embodiment of a light microscope according to the invention.

FIG. 1 shows an embodiment of a light microscope 100 according to the invention. Essential components of the light microscope 100 are: a polychromatic light source 10 to emit illuminating light 15, a structured element 30, with which a spatial structure is imprinted on the illuminating light 15, and focussing means 50 to focus the illuminating light 15 onto a specimen 60. Furthermore the light microscope 100 comprises a detection unit 80, with which specimen light 16 emitted by the specimen 60 in the direction of the focussing means 50 is detected. The specimen light 16 can in particular be illuminating light 15 which is reflected and/or scattered at the specimen 16. In principle the specimen light 16 can, however, also be fluorescent or phosphorescent light which is irradiated as a consequence of the absorption of illuminating light through the specimen.

The light source 10 can comprise for example one or more lasers, a halogen lamp or a diode. The irradiated illuminating light 15 can have a comparatively broad wavelength range and is guided with optical imaging means 12, for example with one or more lenses, to a wavelength selection unit 20.

The wavelength selection unit 20 can comprise an AOTF or one or more prisms, gratings or colour filters. The wavelength selection unit 20 can be operated with electronic control means 90 for sequential selection of narrow-band wavelength ranges of the illuminating light 15.

The portion of the illuminating light 15 selected with the wavelength selection unit 20 is then guided to a deflection means 25. This can for example have a galvanometer mirror or another switchable mirror. Alternatively, the deflection means can also comprise an acousto-optic deflector. The electronic control means 90 are adapted to carry out at least two different adjustments of the deflection means 25, wherein the illuminating light 15 is electively deflected onto a first light path 17 or a second light path 18.

On the first light path 17, the illuminating light 15 is guided onto a mirrored side of the structured element 30. An optical fibre 27 is used for this purpose in the embodiment shown. The illuminating light 15 is in-coupled via a lens 26 into the optical fibre 27, and illuminating light leaving the optical fibre 27 is guided via a further lens 28 onto a beam splitter 29, for example a semi-transparent mirror, and thus further onto the mirrored side of the structured element 30.

On the second light path 18, the illuminating light is in-coupled with a lens 21 into an optical fibre 22 and is guided at the other end of the optical fibre with a lens 23 onto another side of the structured element 30 which is not mirrored.

Instead of optical fibres, the illuminating light 15 can, however, also be guided on the two light paths 17, 18 solely with mirrors and/or lenses. In addition, polarisation filter means can also be present to polarise the illuminating light 15.

The illuminating light 15 can be transmitted on the second light path 18 through the structured element 30, wherein a structure is imprinted on the illuminating light 15, with which it can also be described as structured illuminating light.

The structured element 30 is located in a field plane which is conjugated with a specimen plane so that the structured element 30 is sharply imaged at the specimen plane.

The structured element 30 can be for example a one-dimensional or two-dimensional grating structure. If the two light paths 17, 18 are sequentially used, two phases of the structured element 30 can be imaged one after the other at the specimen location. In order to image further phases of the structured element 30 on the specimen 60, the electronic control means 90 are adapted to displace the structured element 30 in the direction of the double arrow, that is to say: transversely to an optical axis of the light microscope 100, and/or to rotate the structured element 30. By using the two light paths 17, 18, the number of positions of the structured element 30 required for the measurement can advantageously be reduced.

By means of the beam splitter 29, illuminating light 15 of the first light path 17 which is reflected at the structured element and illuminating light 15 of the second light path 18 which is transmitted at the structured element 30 are guided on the same optical path to the specimen 60.

The illuminating light 15 hereby travels through further optical imaging means 31 and also through a beam splitter 40. Illuminating light 15 travelling towards the specimen 60 and specimen light 16 coming from the specimen 60 are separated with the beam splitter 40. For this, the beam splitter 40 can be designed as a polarisation beam splitter 40. In this case, means for changing the polarisation direction of light, for example a λ/4 plate 41, are present between the polarisation beam splitter 40 and the specimen 60. Through the λ/4 plate, the polarisation direction of the illuminating light 15 is rotated on the way to the specimen 60 and the polarisation direction of the specimen light 16 travelling back is rotated once again. The polarisation directions of the illuminating light 15 and the specimen light 16 thereby differ by 90° at the beam splitter, so that efficient separation is possible.

Focussing means 50 are present to focus the illuminating light 15 onto the specimen 60. These comprise here a diffractive element 48 which has a longitudinal chromatic aberration, and also an objective 49. Alternatively, the diffractive element 48 can also be a component of the objective 49. On account of the longitudinal chromatic aberration the focal position of the illuminating light 15 along the optical axis depends upon the wavelength of the illuminating light 15. FIG. 1 shows three different focuses 51 for different wavelengths of the specimen light 16.

By evaluating light of different wavelengths separately, different depths, that is to say: different sections along the optical axis, can be examined. A height profile of the specimen 60 can thereby be created. In the case of a partially transparent specimen, an examination within the specimen can also be realised at different depths.

Specimen light 16 emitted back by the specimen 60 is guided at the polarisation beam splitter 40 into a detection channel, in which it passes via a polarisation filter 42 and optical imaging means 43 onto the detection unit 80. Stray light with a different polarisation direction can be filtered out by the polarisation filter 42.

In order to examine different depths in the specimen 60, tuning of the wavelength of the illuminating light 15 can be carried out, in particular by means of the wavelength selection unit 20, and/or with spectral filtering means at the detection unit 80. To this end, the electronic control means 90 are adapted to tune the wavelength of the light to be detected with the wavelength selection unit 20 and/or the spectral filtering means at the detection unit 80 in order to achieve scanning of the specimen in z-direction without displacement of the specimen 60 being necessary.

Sequentially changing the wavelength of both the illuminating light guided onto the specimen and also the specimen light guided with the filter means onto the detection unit 80 can be advantageous if an adjustable bandwidth of wavelength ranges of the light source cannot be realised with the desired spectral resolution and/or if a spectral resolution of the detection unit, for example using a limited number of colour filters, does not lead to the desired resolution. In this case, an increased spectral resolution can be achieved by a certain wavelength range being selected at the light source in addition with a wavelength filtration being realised at the detection unit. This embodiment can also be advantageous when the imaging of different grating phases is realised through a colour encoding.

A height profile of the specimen 60 can be determined by a respective modulation contrast being determined for the different wavelengths for image points which are adjacent in an xy-plane, thus transversely to the optical axis. The modulation contrast is thereby most marked at the wavelength, of which the z-focus position coincides with the specimen surface. A z-focus position is stored in a value table for each wavelength such that a position of the specimen surface can be determined in z-direction from the determined wavelengths.

The height profile of the specimen 60 can also be determined in a different way than with the modulation contrast. A cross-sectional image of the specimen can be calculated for each wavelength from the plurality of images for different grating phases of the structured element 30. A determination of the height profile can then be realised by selecting, from image points that correspond to each other in their position in the different cross-sectional images, the image point with the greatest intensity or the greatest contrast.

The detection unit 80 comprises a smart pixel array detector in order to take into calculation the images for different grating phases. In order to reduce the measurement time it can additionally be provided that the grating phases are imaged onto the specimen through a polarisation encoding of the illuminating light.

In addition or alternatively to the displacement of the structured element 30, a manipulation of the structured illuminating light 15 in a pupil plane of the objective 50 can also be realised. A grating of the structured element 30 is represented according to the Fourier transformation in the pupil plane essentially as a point pattern which corresponds to the individual orders of diffraction of the grating. Deflection means, for example an electro-optic modulator, an acousto-optic deflector or a galvanometer mirror, can be arranged in the pupil plane. An angular modulation of the illuminating light which corresponds in the pupil plane to a point pattern can hereby be realised, with which it is likewise possible to switch between different grating positions without displacement or rotation of the structured element 30 being necessary.

Alternatively, the structured element 30 can also be formed with a two-dimensional pinhole array instead of the grating. In this case, only the light path 18 is used. The detector elements of the detection unit 80 can thereby be used as a digital pinhole, whereby only the regions of the different images of the specimen sharply imaged onto the detection elements are used to create a confocal image.

Figure 2:
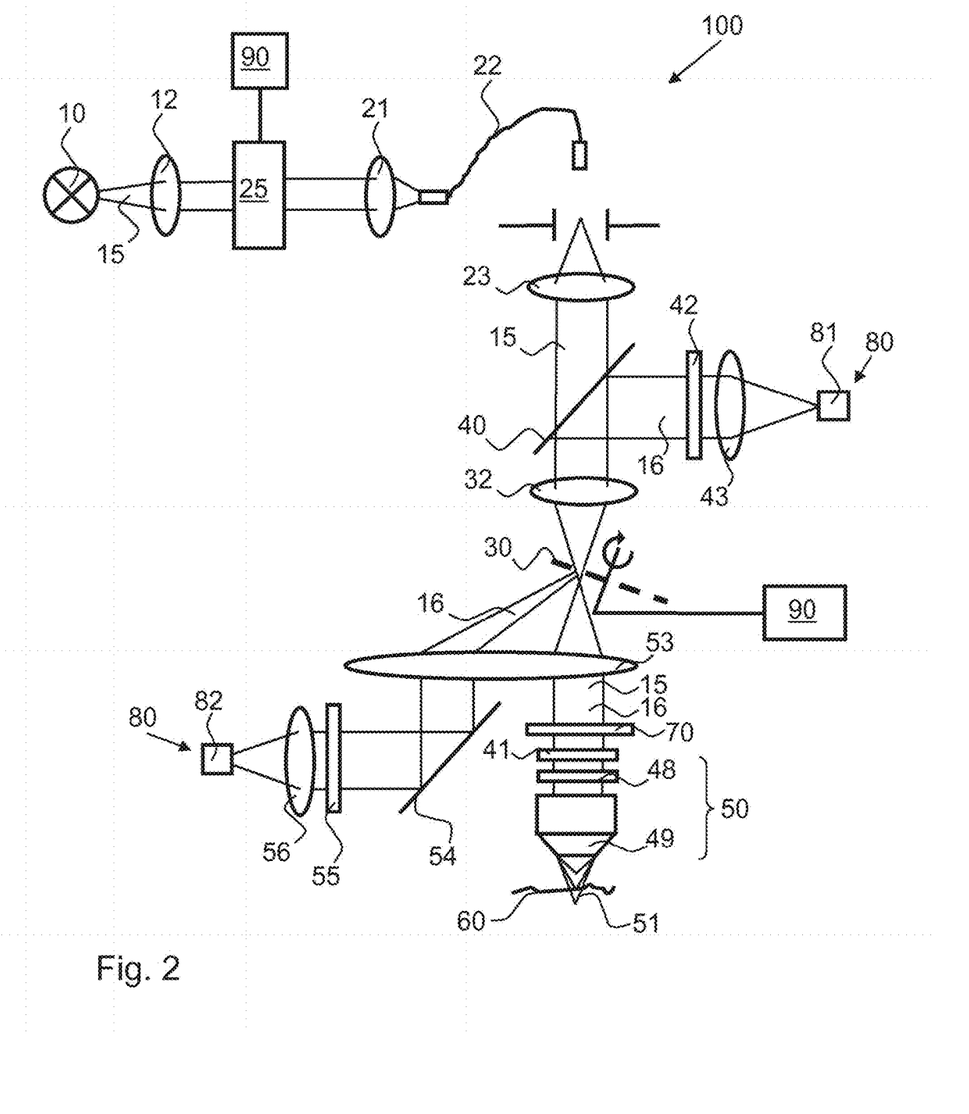
FIG. 2 shows a schematic illustration of a second embodiment of a light microscope according to the invention.

A further embodiment of a light microscope 100 according to the invention is shown schematically in FIG. 2. Once again, illuminating light 15 of the light source 10 is guided onto a structured element 30, for which optical imaging means 32 as well as the components 12, 25, 90, 21, 22, 23 and 40 are used which have already been described in relation to FIG. 1.

Illuminating light 15 transmitted through the structured element 30 is guided, here also, via a λ/4 plate and focussing means 50 onto the specimen 60.

Unlike FIG. 1, however, the beam splitter 40 is not located here between the structured element 30 and the specimen 60, but instead between the light source 10 and the structured element 30. As a result, specimen light 16 leaving the specimen travels through the focussing means 50 and is imaged sharply onto the structured element 30 via optical imaging means 53. The structured element 30 is rotated through the electronic control means 90 and respective images of the specimen are recorded with the detection unit 80 at different rotation positions. A side of the structured element 30 which faces the specimen 60 is mirrored. Specimen light 16 is hereby partially reflected and partially transmitted at the structured element 30.

The transmitted specimen light 16 is spatially separated from the illuminating light 15 with the beam splitter 40 and is detected with a first detector 81 of the detection unit 80. The structuring of the structured element 30 as a pinhole can hereby serve for confocal imaging. Specimen light 16 which is transmitted at the structured element 30 thereby has solely confocal portions. Non-confocal light portions are filtered out at the structured element 30. The detector 81 can thereby record a confocal image of the specimen 60.

Illuminating light 16 which is reflected at the structured element 30 has on the other hand both confocal and also non-confocal portions. The reflected specimen light 16 is then imaged via optical imaging means 53, a deflection mirror 54, a polarisation filter 55 and via further optical imaging means 56 onto a second detector 82 of the detection unit 80. The second detector 82 thereby records a wide-field image of the specimen 60 which contains image information from different depths and not only from the focal position of the illuminating light 15.

A depth resolution is also realised in this embodiment via the wavelength-dependent focal position 51 of the illuminating light 15.

In the example shown, the two detectors 81 and 82 are formed through separate camera chips. Alternatively, however, a single camera chip can also be used, wherein the two detectors 81 and 82 represent different regions of the camera chip.

The depth resolution, thus the resolution along the optical axis at the specimen 60, can be increased by measuring with better spectral resolution. An interferometer 70 is present for this purpose according to a further embodiment of a light microscope 100 according to the invention, which is shown in a cut-out in FIG. 3. By way of an optional extension, the interferometer 70 is also shown in FIGS. 1 and 2 between the focussing means 50 and the structured element 30.

Figure 3:
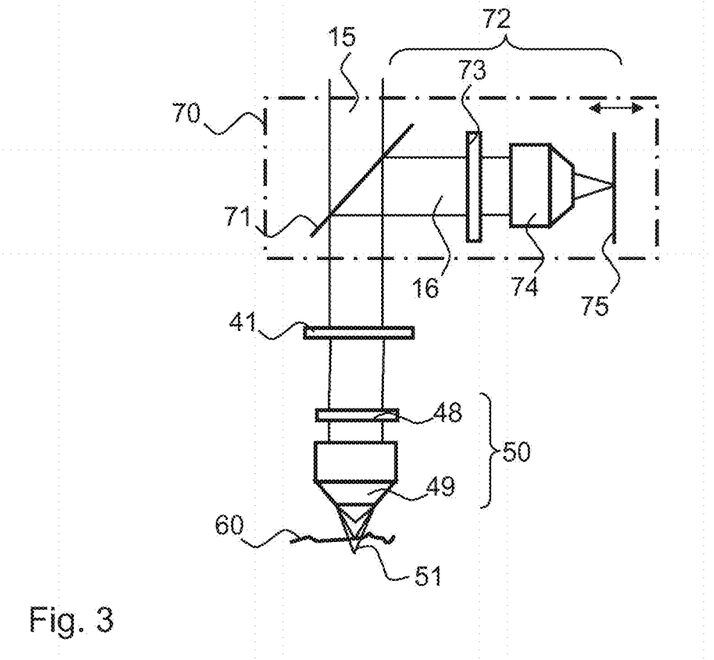
FIG. 3 shows a schematic illustration of a part of a further embodiment of a light microscope according to the invention.

The interferometer 70 is designed here as a Linnik interferometer. It comprises a beam splitter 71, with which a proportion of the specimen light 16 is guided onto a reference path 72. On the reference path 72 there is a, preferably achromatic, objective 74 and also a mirror 75 which is arranged in the focus of the objective 74 and radiates specimen light 16 leaving the objective 74 back thereto. Optionally, the mirror 75 can also be moved via the electronic control means 90. By displacing the mirror 75 the length of the reference path 72 and hence the path difference required for the spectral interferometry can be adjusted.

Furthermore a λ/4 plate 73 can be present between the beam splitter 71 and the objective 74 in order to rotate the polarisation direction of the specimen light 16.

Illuminating light 15 which is transmitted at the beam splitter 71 travels, as described in relation to FIG. 1, via a λ/4 plate 41 and the focussing means 50 onto the specimen 60.

Further information going beyond the chromatic information can advantageously hereby be obtained which can be used in relation to a height evaluation of the specimen. Indeed, the path difference which is to be adjusted with the interferometer 70 for a specified wavelength depends upon the distance of the specimen surface and hence upon the height profile of the specimen. The position of the mirror 75, with which a path difference for constructive interference at the specimen surface is adjusted, can likewise be used to determine the height profile.

The detected light should hereby be measured with a spectral resolution in the order of 0.1 nm, which is not possible solely with a simple colour camera as a detection unit. It is thus preferable to use a tunable light source together with a spectrally resolving detection unit.

Much information for a microscopic specimen can be obtained with the light microscope according to the invention. In particular, a confocal image and also a wide-field image of the specimen can thereby be recorded without the need to reorganise or remove components from the light microscope. Scanning of the specimen through mechanical displacement of components can be mostly omitted. Different xy-points of the specimen can thus be examined using structured illuminating light, whereby no repositioning of components is required or, at most, an adjustment of the structured element is necessary. A z-resolution is produced with the aid of a longitudinal chromatic aberration, wherein the z-resolution depends upon the measurement accuracy of the wavelength of the light to be detected. The wavelength can be determined particularly exactly in variants, in which the light source is tunable and the detection unit is additionally spectrally resolving.

LIST OF REFERENCE SIGNS

10 Light source
12 Optical imaging means, lens
15 Illuminating light
16 Specimen light
17 First light path
18 Second light path
20 Wavelength selection unit
21 Lens
22 Optical fibre
23 Lens
25 Deflection means
26 Lens
27 Optical fibre
28 Lens
29 Semi-transparent mirror
30 Structured element
31 Optical imaging means, lens
32 Optical imaging means, lens
40 Beam splitter, polarisation beam splitter
41 λ/4 plate
42 Polarisation filter
43 Optical imaging means, lens
48 Diffractive element with longitudinal chromatic aberration
49 Objective
50 Focussing means
51 Focus of the illuminating light
53 Optical imaging means, lens
54 Deflection mirror
55 Polarisation filter
56 Optical imaging means, lens
60 Specimen
70 Interferometer
71 Beam splitter
72 Reference path
73 λ/4 plate
74 Achromatic objective
75 Mirror
80 Detection unit
90 Electronic control means
100 Light microscope

The invention claimed is:

1. A light microscope, comprising
a polychromatic light source for emitting illuminating light in the direction of a specimen,
focusing means for focusing illuminating light onto the specimen, wherein the focusing means have a longitudinal chromatic aberration to produce a depth resolution,
a structured element arranged between the light source and the focusing means to produce structured illuminating light from the illuminating light emitted by the light source, and
a detection unit which comprises a two-dimensional array of detector elements for detecting specimen light coming from the specimen, wherein
for the detection of both confocal portions and also non-confocal portions of the specimen light, an optical path from the specimen to the detection unit is free of elements for complete filtering-out of non-confocal portions,
wherein specimen light coming from the specimen is guided through the structured element onto the detection unit, wherein structures of the structured element are sufficiently large for the passage of non-confocal portions of the specimen light,
wherein the structures of the structured element are larger than one Airy disc, and the optical path from the specimen to the detection unit is free of elements that have structures for leading specimen light to the detection unit which are smaller than one Airy disc to obtain both confocal information and wide-field information through a single measurement or a single measurement sequence, whereby confocal and wide-field information are obtained
simultaneously or
one after another without mechanical movements of components of the light microscope to switch between obtaining confocal and wide-field information.

2. The light microscope according to claim 1,
wherein the structured element comprises a Nipkow disc, a microlens array, a grating, a Fresnel bi-prism or an element for generating a speckle pattern.

3. The light microscope according to claim 1,
wherein the focusing means comprise at least one of: a light refractive or a light diffractive microlens array to produce a wavelength-dependent focal position.

4. The light microscope according to claim 1,
wherein a wavelength selection unit is present to select a variably adjustable spectral range of the illuminating light in order to focus via the focusing means illuminating light onto different positions along an optical axis of the light microscope, and electronic control means are present to select a spectral range by means of the wavelength selection unit.

5. The light microscope according to claim 4,
wherein the wavelength selection unit comprises at least one of: a prism, a grating, a colour filter or an acousto-optic tunable filter.

6. The light microscope according to one of claim 1, wherein
a deflection means is present for selective guiding of illuminating light onto a first or a second light path,
the structured element is mirrored on one side,
wherein illuminating light of the first light path is guided onto the mirrored side of the structured element and is reflected at the structured element in the direction of the specimen, and
wherein illuminating light of the second light path is guided onto a different side of the structured element and transmitted by the structured element in the direction of the specimen, and
wherein the transmitted illuminating light and the reflected illuminating light produce images of the structured element, phase displaced with respect to each other, on the specimen.

7. The light microscope according to claim 6,
wherein the deflection means comprises at least one of: a switchable mirror, an acousto-optic modulator, an acousto-optic deflector, an electro-optic modulator or a switching unit based upon polarization direction.

8. The light microscope according to claim 1, wherein
positioning means for at least one of: displacing or rotating the structured element are provided and electronic control means are provided which are adapted, with the detection unit, to record images of the specimen at different positions of the structured element and to calculate a specimen image from these images.

9. The light microscope according to claim 1, wherein the detection unit is a spectrally resolving detection unit.

10. The light microscope according to claim 9, wherein spectral filtering means are provided to produce the spectral resolution of the detection unit, or the detection unit comprises an interferometer.

11. A method for recording images with a light microscope, comprising:
transmitting illuminating light with a polychromatic light source in the direction of a specimen,
guiding the illuminating light to a structured element to produce structured illuminating light,
focusing the structured illuminating light onto the specimen with focusing means, wherein a depth resolution is achieved through a longitudinal chromatic aberration of the focusing means,
guiding specimen light coming from the specimen through the structured element to a detection unit which comprises a two-dimensional array of detector elements,
guiding both confocal portions and also non-confocal portions of the specimen light onto the detection unit,
wherein structures of the structured element are sufficiently large for the passage of non-confocal portions of the specimen light, wherein the structures of the structured element are larger than one Airy disc, and
wherein both confocal information and wide-field information are obtained through a single measurement or a single measurement sequence
simultaneously or
one after another without mechanical movements of components of the light
microscope to switch between obtaining confocal and wide-field information,
by providing the optical path from the specimen to the detection unit to be free of elements that have structures for leading specimen light to the detection unit which are smaller than one Airy disc.

12. The method according to claim 11, wherein
for the determination of a height profile of a specimen, images of the specimen are recorded which differ in the detected wavelength range of the specimen light,
a modulation contrast is determined for image points of each image,
the image point with the greatest modulation contrast is selected from those image points that have the same position in the different images, and
height information of the specimen is assigned to the selected image point in dependence upon the associated wavelength range, wherein respective height information has been previously stored for each of the different wavelength ranges.

13. The method according to claim 11, wherein
the detection unit is arranged in a plane which is conjugated with the specimen plane,
for the production of a confocal image, the detector elements of the detection unit are used as a digital diaphragm, wherein for the purpose of creating a confocal image those detector elements are used onto which specimen regions lying in the focus of the illuminating light are sharply imaged.

14. The method according to claim 11, wherein
with an interferometer, a part of the specimen light is guided onto a reference path with adjustable length and subsequently guided back onto the specimen,
wherein a constructive interference on a surface of the specimen between illuminating light and specimen light guided back depends upon a height profile of the specimen and also upon the length of the reference path,
the length of the reference path is varied and the length, at which a maximum signal is received with the detection unit, is selected,
the height profile of the specimen is concluded from the selected length of the reference path with the aid of previously stored values.

15. The method according to claim 11, wherein for the improvement of the spectral resolution, a wavelength selection is realized both via spectral filtering means of the detection unit and also via a wavelength selection unit at the light source.

16. The method according to claim 11, wherein
a first image of the specimen is recorded, wherein a structured element is located in the optical path to produce a structured illumination,
a second image is recorded for the examination of specimen regions that were not illuminated with the structured illumination when recording the first image, wherein the structured element is not located in the optical path, and
a specimen image is calculated from the first and the second image.

17. The method according to claim 11, wherein a polarization encoding of at least one of: illuminating light or specimen light is realized for improving a measurement resolution in a specimen plane lying transversely to an optical axis,
wherein regions lying one beside the other in the specimen plane are irradiated with illuminating light of different polarizations, or wherein a position-dependent specimen light polarization is realized, wherein a certain polarization is imprinted on specimen light in dependence upon its position transversely to the optical axis,
wherein specimen light is detected separately for different polarizations, and
wherein position information within the specimen plane is assigned to the detected specimen light in dependence upon its polarization.

18. A light microscope, comprising:
a polychromatic light source for emitting illuminating light in the direction of a specimen,
focusing means for focusing illuminating light onto the specimen, wherein the focusing means have a longitudinal chromatic aberration to produce a depth resolution,
a structured element arranged between the light source and the focusing means to produce structured illuminating light from the illuminating light emitted by the light source, and
a detection unit which comprises a two-dimensional array of detector elements for detecting specimen light coming from the specimen, wherein for the detection of both confocal portions and also non-confocal portions of the specimen light, an optical path from the specimen to the detection unit is free of elements for complete filtering-out of non-confocal portions, the structured element is partially mirrored on one side to split incoming specimen light into a confocal beam path formed by specimen light transmitted at the structured element and including only confocal light portions and a non-confocal beam path formed by specimen light reflected at the structured element and including at least non-confocal light portions, the detection unit has a first and a second detector, the first detector is arranged in the confocal beam path and the second detector is arranged in the non-confocal beam path.

* * * * *